US008556898B2

(12) United States Patent
Graf et al.

(10) Patent No.: US 8,556,898 B2

(45) Date of Patent: Oct. 15, 2013

(54) ACCESSORY FOR IMPLANTING A HIP ENDOPROSTHESIS, AND METHOD FOR MANIPULATING THE SAME

(75) Inventors: Reinhard Graf, Murau (AT); Martin Imhof, Rotkreuz (CH); Rene Brack, Rotkreuz (CH)

(73) Assignee: Smith and Nephew Orthopaedics AG, Rotkreuz (CH)

( * ) Notice: Subject to any disclaimer, the term of this patent is extended or adjusted under 35 U.S.C. 154(b) by 424 days.

(21) Appl. No.: 12/899,955

(22) Filed: Oct. 7, 2010

(65) Prior Publication Data

US 2011/0087230 A1 Apr. 14, 2011

Related U.S. Application Data

(62) Division of application No. 10/501,004, filed as application No. PCT/EP03/00035 on Jan. 3, 2003, now Pat. No. 7,828,806.

(30) Foreign Application Priority Data

Jan. 10, 2002 (DE) ................................. 102 00 690

(51) Int. Cl.
*A61B 17/00* (2006.01)

(52) U.S. Cl.
USPC ............................................... 606/81; 606/91

(58) Field of Classification Search
USPC ............ 606/81, 91; 623/22.11–22.22, 22.15, 623/22.21
See application file for complete search history.

(56) References Cited

U.S. PATENT DOCUMENTS

| | | | | |
|---|---|---|---|---|
| 4,224,698 | A | | 9/1980 | Hopson |
| 4,305,394 | A | | 12/1981 | Bertuch |
| 4,475,549 | A | | 10/1984 | Oh |
| 4,528,980 | A | | 7/1985 | Kenna |
| 4,716,894 | A | | 1/1988 | Lazzeri et al. |
| 4,987,904 | A | | 1/1991 | Wilson |
| 5,037,424 | A | | 8/1991 | Aboczsky |
| 5,098,437 | A | | 3/1992 | Kashuba et al. |
| 5,474,560 | A | | 12/1995 | Rohr, Jr. |
| 5,571,111 | A | | 11/1996 | Aboczky |
| 5,616,147 | A | * | 4/1997 | Gadelius ....................... 606/102 |
| 5,658,347 | A | * | 8/1997 | Sarkisian et al. .......... 623/22.22 |
| 6,102,915 | A | | 8/2000 | Bresler et al. |
| 6,231,611 | B1 | | 5/2001 | Mosseri |
| 6,395,005 | B1 | * | 5/2002 | Lovell ............................ 606/91 |
| 6,565,575 | B2 | | 5/2003 | Lewis |
| 6,743,235 | B2 | | 6/2004 | Subba Rao |
| 6,905,502 | B2 | * | 6/2005 | Penenberg ...................... 606/81 |
| 2001/0012967 | A1 | | 8/2001 | Mosseri |

(Continued)

OTHER PUBLICATIONS

European Office Action; European Patent Application No. 03 702 385.0; Aug. 21, 2007; 3 pages.

*Primary Examiner* — Nicholas Woodall

(74) *Attorney, Agent, or Firm* — Krieg DeVault LLP

(57) ABSTRACT

The application relates to a method of orienting a bone-milling cutter and an impact instrument for a hip-prosthesis cup in an acetabulum. The method includes initially positioning a manipulation cup by a manipulation joint head and representing this position by at least one guide rod or fixation rod that is fixed in a bone. The method also includes removing the manipulation cup and adjusting a position of both the bone-milling cutter and the impact instrument with respect to either the guide rod itself or a guide rod that is attached to a holding device disposed on at least one fixation rod.

20 Claims, 15 Drawing Sheets

18 29 17 30 41 42 36 24 31 40 37 38 32 39

(56) References Cited

U.S. PATENT DOCUMENTS

| | | | | |
|---|---|---|---|---|
| 2002/0116007 | A1 | 8/2002 | Lewis | |
| 2003/0050645 | A1 | 3/2003 | Parker et al. | |
| 2003/0153829 | A1 | 8/2003 | Sarin et al. | |
| 2003/0229356 | A1 | 12/2003 | Dye | |
| 2004/0097952 | A1 | 5/2004 | Sarin et al. | |
| 2006/0161167 | A1 * | 7/2006 | Myers et al. | 606/91 |
| 2006/0184177 | A1 * | 8/2006 | Echeverri | 606/91 |
| 2007/0270783 | A1 | 11/2007 | Zumsteg et al. | |
| 2009/0099665 | A1 * | 4/2009 | Taylor et al. | 623/22.21 |
| 2010/0121335 | A1 * | 5/2010 | Penenberg et al. | 606/91 |

* cited by examiner

ACCESSORY FOR IMPLANTING A HIP ENDOPROSTHESIS, AND METHOD FOR MANIPULATING THE SAME

CROSS REFERENCE TO RELATED APPLICATIONS

This application is a divisional of U.S. application Ser. No. 10/501,004 filed on Dec. 13, 2004, which issued as U.S. Pat. No. 7,828,806 on Nov. 9, 2010, which is a U.S. National Phase Application of PCT/EP03/00035 filed Jan. 3, 2003 designating the U.S. and published in German on Jul. 17, 2003 as WO 03/057087, which claims priority to German Application No. 102 00 690.3 filed Jan. 10, 2002. The disclosures of these applications are incorporated by reference herein in their entirety.

FIELD OF INVENTION

The invention relates to an accessory for implantation of a hip joint endoprosthesis, as well as to a method for manipulating it, in particular for orienting a bone-milling cutter and an impact instrument to implant a prosthesis cup in the acetabulum.

BACKGROUND

When hip endoprostheses are being inserted, the surgeon must proceed through various stages of the operation in which tools are employed; in particular, it is necessary to use a bone cutter in order to mill out the natural acetabulum and thus form a bearing socket within which an artificial cup can be anchored. An impact instrument is also used to drive the cup into place. When using either tool the surgeon must take care that the tools are oriented as precisely as possible, so that the prosthesis cup will ultimately be positioned as intended, with the greatest possible precision.

Important accessories that assist correct positioning and orientation of the tools include so-called navigation systems that function with computer assistance. Obviously, such systems are quite elaborate, and the costs of employing them are correspondingly high. In view of the fact that in medicine, as elsewhere, it is important to reduce costs without any deterioration in the quality of medical care, the present invention is directed toward the objective of providing an accessory for the implantation of a hip joint endoprosthesis that allows exact positioning of the prosthesis cup in relation to the femur, specifically to the joint head anchored in the femur, with simple mechanical means. During this operation care must be taken to implant the cup in such a way that during every conceivable movement of the femur, a collision between the edge of the cup and the neck of the femur is avoided.

SUMMARY OF THE INVENTION

This objective is achieved in accordance with the invention by an accessory that comprises the following basic elements: Manipulation cup Manipulation joint head with means for orienting the manipulation cup in the acetabulum, and Device to represent the correctly oriented position of the manipulation cup, so that by means of this device it is then possible to orient appropriately a bone-milling cutter and an impact instrument, which are used for placement of the prosthesis cup.

The central point of the accessory in accordance with the invention is thus that by means of a manipulation joint head the manipulation cup is put into a position within the acetabulum such that for all conceivable movements of the femur, a collision between the cup edge and the femoral neck is ruled out. For this purpose, the manipulation joint head is provided with appropriate mechanical or optical orientation means. In a first preferred exemplary embodiment the orientation means is constructed in the form of a shoulder that extends radially outward beyond the spherical part of the manipulation joint head. This shoulder corresponds to the rim of the manipulation cup when the latter is correctly oriented in the acetabulum. When the femur is in its “zero position”, the shoulder on the manipulation joint head is spaced apart from the rim of the manipulation-cup opening by an approximately uniform amount over the entire circumference of the latter. The manipulation joint head is fixed to the neck of a manipulation rasp, in particular is set onto it, to assist orientation of the manipulation cup. The manipulation rasp itself is fixed within the femur. Subsequently the operator causes the femur to make all conceivable movements, as follows: Flexion/extension about the “mediolateral” axis Abduction/adduction about the “anterior/posterior” axis Inward/outward rotation about the “craniocaudal” axis.

During this movement sequence the collisions that occur between the shoulder of the manipulation joint head and the rim of the manipulation cup cause the manipulation cup to move into a position such that, after the final implantation of the hip-joint endoprosthesis, collision between the rim of the prosthesis cup and the femoral neck will be reliably avoided.

Another device will of course be needed to represent the position in which the manipulation cup is correctly oriented, after the latter has been removed. With this device it is then possible to orient a bone-milling cutter and an impact instrument for positioning the prosthesis cup within the socket that has been milled out in the acetabulum.

The above-mentioned shoulder on the manipulation joint head can also be defined by shoulder sections distributed approximately uniformly over the circumference of the head. In the extreme case these sections can also be replaced by peg-like projections. Naturally, there must then be a sufficient number of these projections to achieve the orientation of the manipulation cup described above.

As a device to represent the correctly oriented position of the manipulation cup, it is preferable to use a guide rod that can be fixed in the bone and corresponds to a guide device disposed on the manipulation cup. The guide rod can be constructed either as a nail or also as a threaded rod. In the latter case the guide rod comprises a screw thread on the end section to be anchored in the bone, so that it can be screwed into the bone (namely the pelvic bone).

The guide device on the manipulation cup that is associated with the guide rod preferably comprises a component connected to the manipulation cup by way of an arm; this component is in particular a guide block or a guide sleeve with a bore within which the guide rod is guided. Accordingly, after the manipulation cup has been oriented, the guide rod is passed through the guide bore in the guide device disposed on the manipulation cup and is anchored in the bone. Then the manipulation cup is detached from the guide rod. This leaves the guide rod free so that a template can be attached thereto, in particular pushed onto it, for orienting a cutting head or its drive axis in such a way that the orientation of the cutting head corresponds to that of the manipulation cup. When only a single guide rod is available, the orienting template is preferably also rotatable about said rod.

In a preferred implementation of the first exemplary embodiment the orienting template comprises an arm, in particular an angled strap, that can be pushed onto the guide rod and at its free end (i.e., the end opposite the guide rod) bears a direction plate, in particular a plate provided with directional marks with which to orient the milling-cutter drive axle; for such orientation said axle is pivoted while in complete, i.e. gap-free contact with the direction plate and where appropriate also parallel thereto. The marks preferably also provided on the direction plate allow the milling-cutter drive axle to be pivoted parallel to the direction plate into a position aligned with a predetermined directional mark, in particular a predetermined zero position. Accompanying this zero position can be marks for two maximal-tolerance positions, namely±5°.

So that the direction plate can be held against the drive axle in a gap-free manner even when the milling cutter is in operation, the cutter drive axle is provided with a bush within which it is rotatably seated, and to which the direction plate can be apposed without a gap even during the milling process.

As already mentioned above, an impact instrument is also provided with which to hammer the prosthesis cup into its final position, in a prespecified orientation. The cup impact instrument can likewise be oriented with respect to the above-mentioned direction plate of the orienting template, in the same way as is the cutting head or its drive axle. Because the cup impact instrument is known per se, there is no need to describe it further here.

The manipulation cup can also be provided with a guide device by means of which two or more guide rods can be fixed in the bone parallel to one another. In this case the orienting template, which positions the cutting head or its drive axle as well as the cup impact instrument, likewise comprises two or three corresponding through-bores so that it can be pushed onto the guide rods fixed in the bone.

Another implementation of the first exemplary embodiment is characterized by a U-shaped curvature of the direction plate on the orienting template, in which case the space between the two limbs of the plate serves as a receptacle for the milling-cutter drive axle. The axle is preferably seated therein substantially without play, i.e. is parallel to the direction plate, so that the operator need only be concerned with adjusting the drive axle to the zero position. In order to better identify this zero position, the limb of the plate toward the operator, in particular the upper limb, can be provided at its end face with recesses that serve as markings for positioning the milling-cutter drive axle parallel to the direction plate.

Another exemplary embodiment of an accessory in accordance with the invention is characterized in that as a means for orienting the manipulation cup in the acetabulum optical identifiers are provided, e.g. in the form of an indentation or groove that extends over the circumference of the spherical part of the manipulation joint head. Instead of an indentation or groove, a marking line can be provided. All such markings extend within a plane that is either perpendicular to the central axis of the joint head or set at a predetermined angle thereto. In the first case the manipulation cup is correctly oriented when the marking becomes visible above the edge of the manipulation cup. In the second case the orientation of the manipulation cup is anatomically correct when the marking is undetectable on all sides, i.e. over the entire circumference of the manipulation cup.

In each case the manipulation joint head is fixed to the neck of a manipulation rasp in such a way that the central axis of the joint head coincides with the neck axis.

In a third exemplary embodiment the means for orienting the manipulation cup in the acetabulum is a circumferential shoulder extending outward from the joint head in a plane perpendicular to the central axis of the head, combined with a receptacle for the neck of a manipulation rasp, which is positioned at an angle to the central axis of the joint head such that its long axis is parallel to the axis of the femoral neck.

In the case of this exemplary embodiment, the manipulation cup is correctly oriented when the circumferential shoulder on the manipulation joint head is flush with the outer annular surface around the circumference of the manipulation cup.

As a device to represent the correct orientation of the manipulation cup, it is also possible to use separate fixation rods that extend through a device for holding the manipulation cup. These fixation rods are provided with helically threaded end sections, which can be screwed into the bone so as to anchor the rod therein. In this case it is preferable for a guide rod to be connectable to the aforementioned holding device, in such a way that the guide rod extends approximately parallel to the central axis of the manipulation cup. Then it is possible to attach to this guide rod a guide element that serves to guide a milling-cutter drive axle or a cup impact instrument. The guide element ensures that the orientation of the cutter drive axle and the impact instrument corresponds to that of the manipulation cup.

Regarding further details of this embodiment, reference is made to the relevant subordinate claims.

In the following, exemplary embodiments of the accessory in accordance with the invention, i.e. an instrument for the orientation of manipulation cups, is explained in greater detail with reference to the attached drawings, which illustrate the following objects and actions:

DETAILED DESCRIPTION

Figure 1:
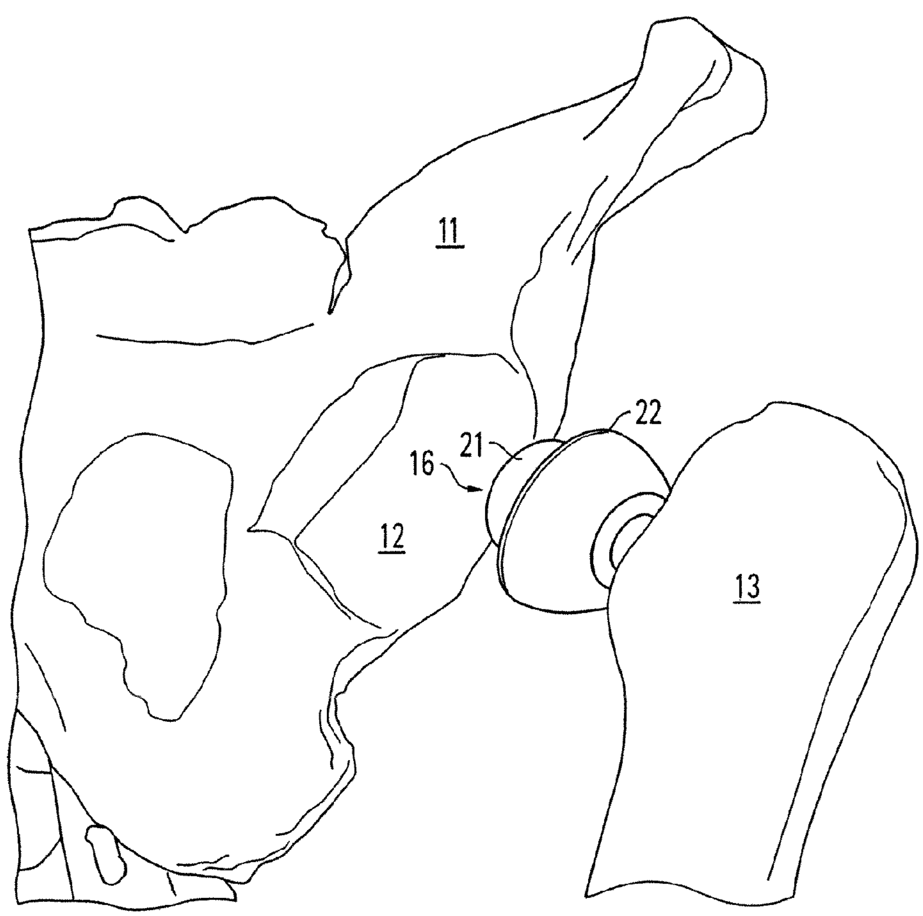
FIG. 1 manipulation joint head fixed to the neck of a manipulation rasp that is placed within the femur, shown in position with respect to the natural acetabulum.
Figure 2:
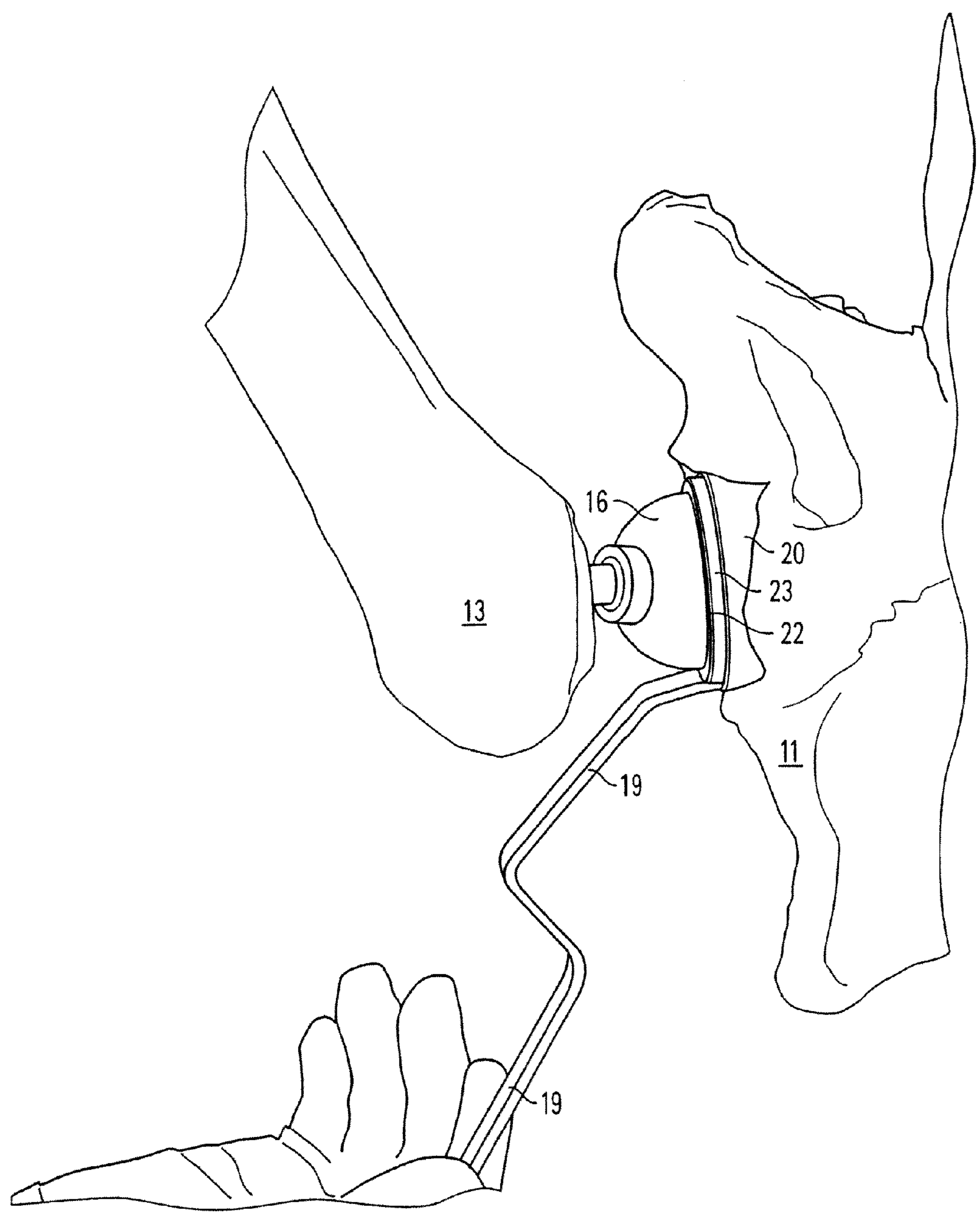
FIG. 2 orienting a manipulation cup placed in the acetabulum by means of the manipulation joint head according to FIG. 1.
Figure 10:
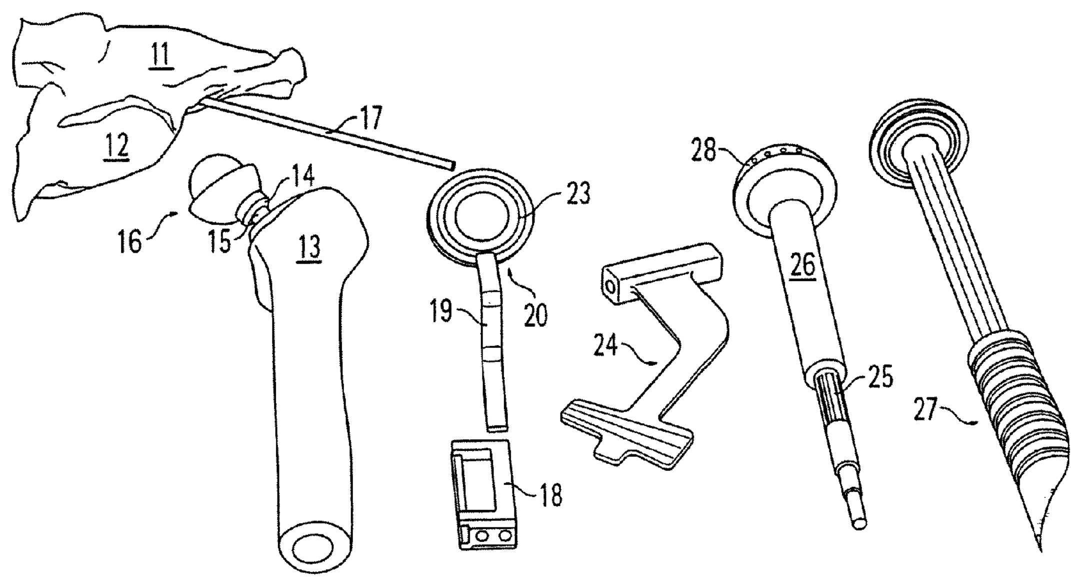
FIG. 10 the complete set of instruments for implantation of a hip joint endoprosthesis, viewed in perspective.

Prior to consideration of the individual steps, for a first exemplary embodiment the complete set of instruments for anatomically correct implantation of a hip joint endoprosthesis will be described with reference to FIG. 10, which shows the following parts (from left to right): 11 Pelvic bone 12 Acetabulum 13 Proximal section of a femur, within which a manipulation rasp (not shown in detail) is fixed 14 Proximal end of the manipulation rasp placed within the femur 15 Prosthesis neck 16 Manipulation joint head set onto the prosthesis neck in the conventional way, in particular by means of a "stick-on cone" connection 17 Guide rod anchored in the pelvic bone 18 Guide block, which can be attached to a manipulation cup to accommodate the guide rod 17 19 Manipulation cup with holder strap 19 for the guide block 18 24 Orienting template 25 Drive axle for milling cutter 26 Axle bush 27 Cup impact instrument 28 Cutting head As shown in FIG. 1, the first step is to tilt the femoral neck back and insert into it, beginning at the plane of resection, a manipulation rasp onto the neck of which a manipulation joint head 16 will be set. The manipulation joint head 16 comprises a spherical part 21, around the circumference of which is a shoulder 22 that extends radially outward. This shoulder 22 is used to establish correspondence with the rim 23 around the opening of the manipulation cup 20, as shown in FIG. 2. In a "zero position" the distance separating the shoulder 22 from the rim 23 of the cup opening is approximately equal around the circumference of the rim 23. Starting from this zero position, the femur 13 together with the manipulation joint head 16 is moved in all anatomically conceivable directions, as described above. As a result of this movement, collisions between the shoulder 22 and the rim 23 of the manipulation cup 20 are very likely to occur at several places, with the consequence that the manipulation cup 20 becomes appropriately oriented within the acetabulum.

Figure 3:
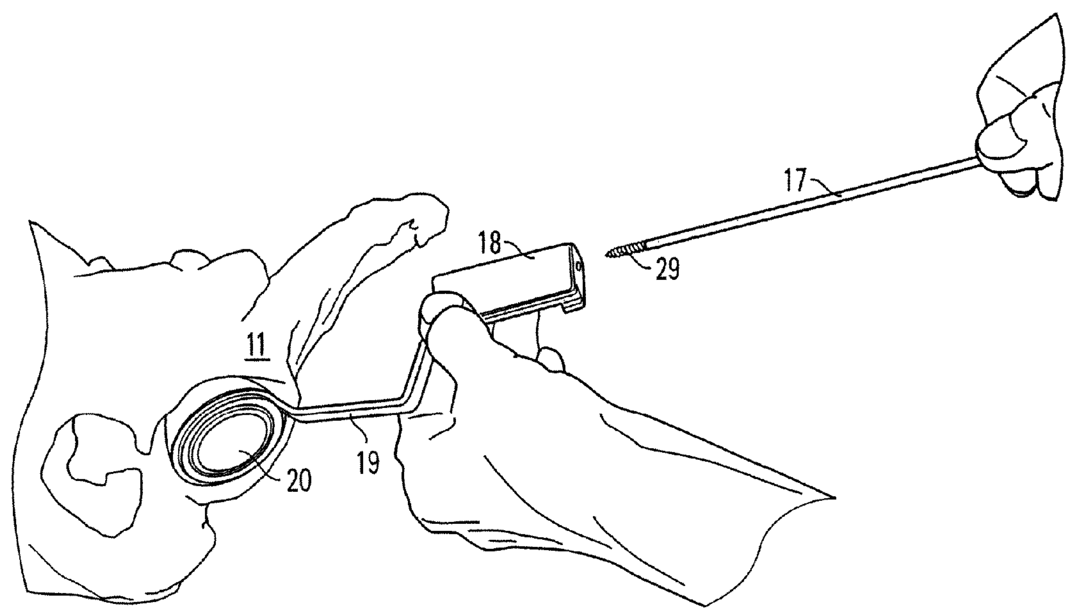
FIG. 3 placement of a guide rod within a guide device associated with the manipulation cup, for future representation of the correct orientation of the manipulation cup, for which purpose the guide rod is anchored in the pelvic bone.
Figure 4:
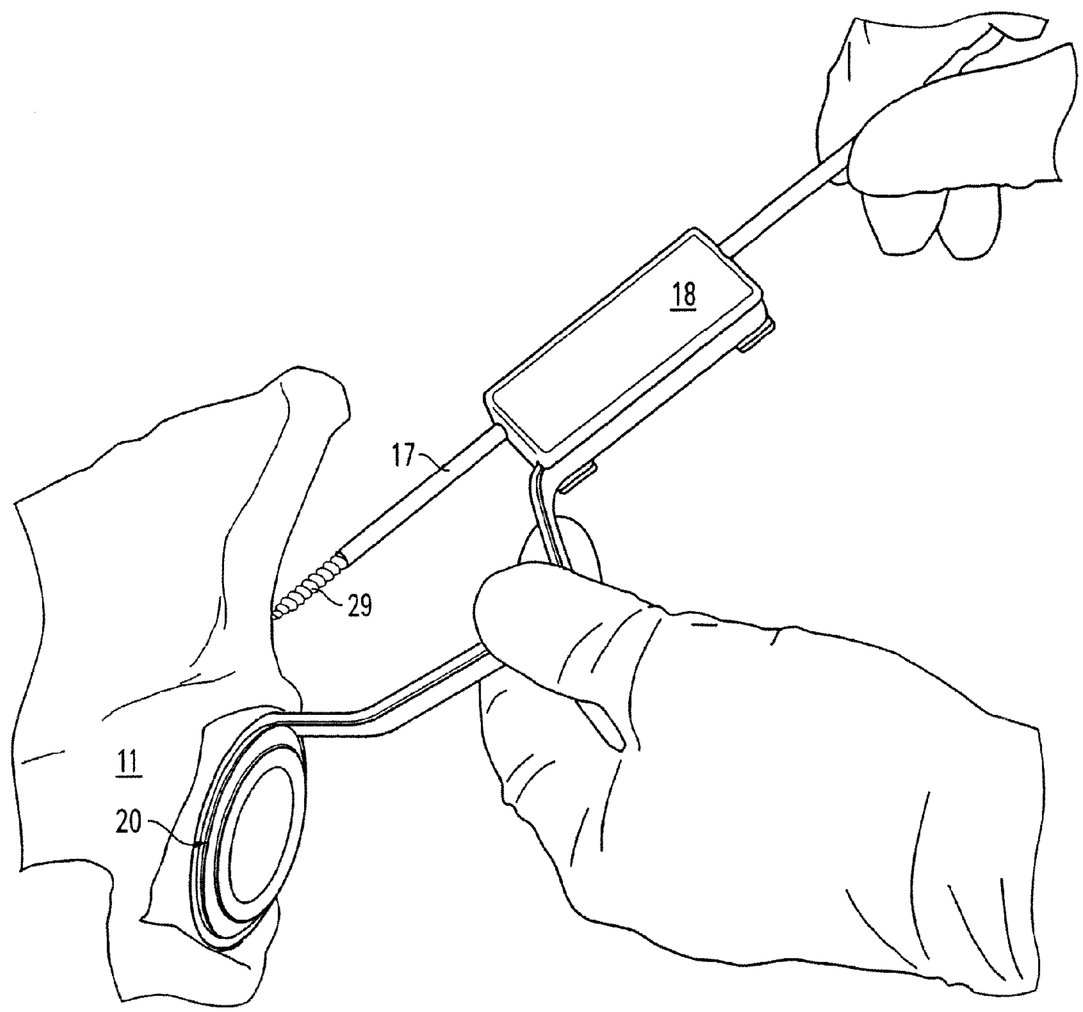
FIGS. 4 and 5 removal of the manipulation cup from the acetabulum and from the guide rod anchored in the bone.
Figure 5:
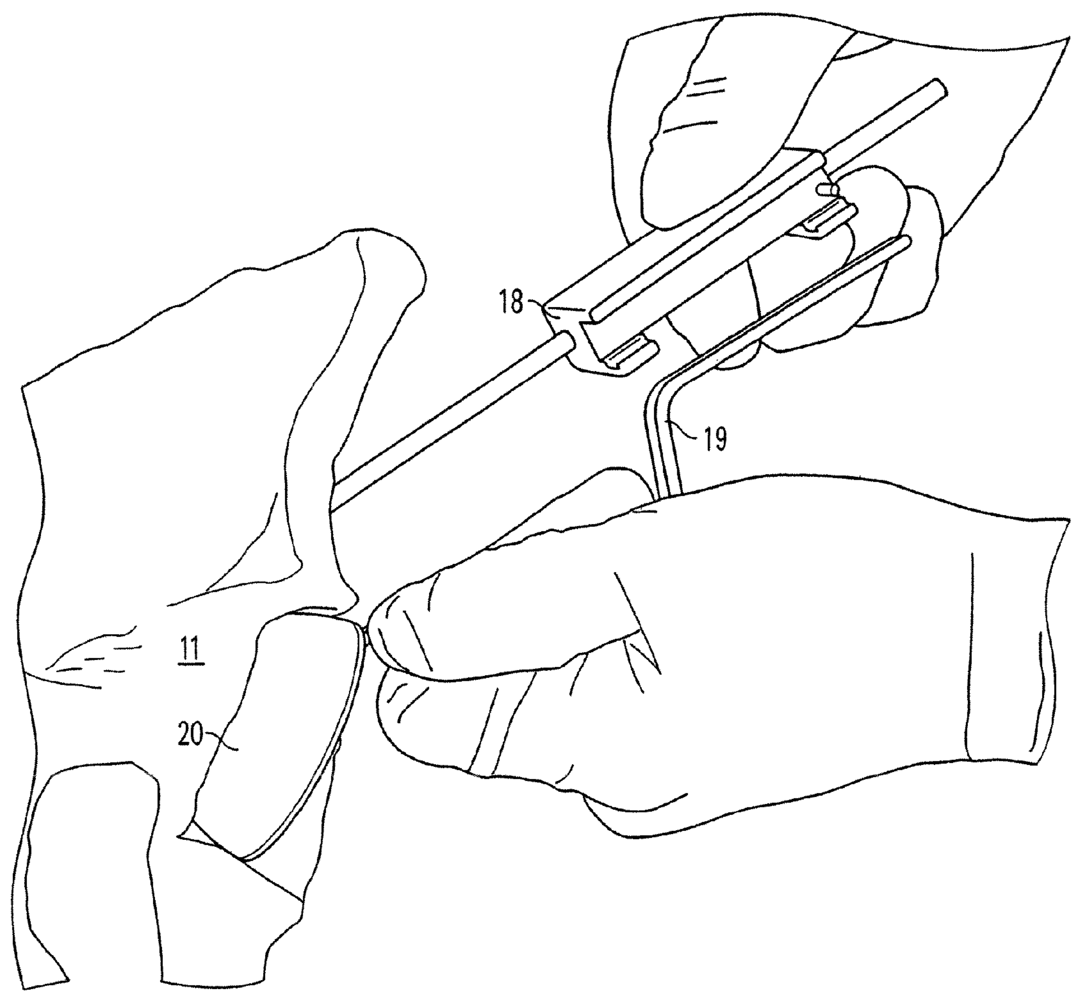

The oriented position of the manipulation cup 20 must be preserved so that both the bone-milling cutter and the impact instrument for the prosthesis cup can be appropriately oriented. For this purpose the manipulation cup 20 is connected by way of a holder strap 19 to a guide device in the form of a guide block 18 comprising a guide bore, the axis of the block being directed toward the pelvic bone 11 and outside the region in which collision with the manipulation cup is possible. Through said guide bore is passed a guide rod 17, as shown in FIGS. 3 and 4. The guide rod 17 has a threaded section 29 at its end that points toward the bone 11, by means of which the guide rod 17 can be screwed into the bone 11 and thus fixed there. The guide rod 17 is, of course, not screwed into the bone 11 until the manipulation cup 20 has been correctly oriented, so that the rod can represent the position of the manipulation cup within the acetabulum. After the guide rod 17 has been fixed within the pelvic bone 11 as just described, the manipulation cup is detached from the guide block 18 as shown in FIG. 5 and removed from the acetabulum.

Figure 6:
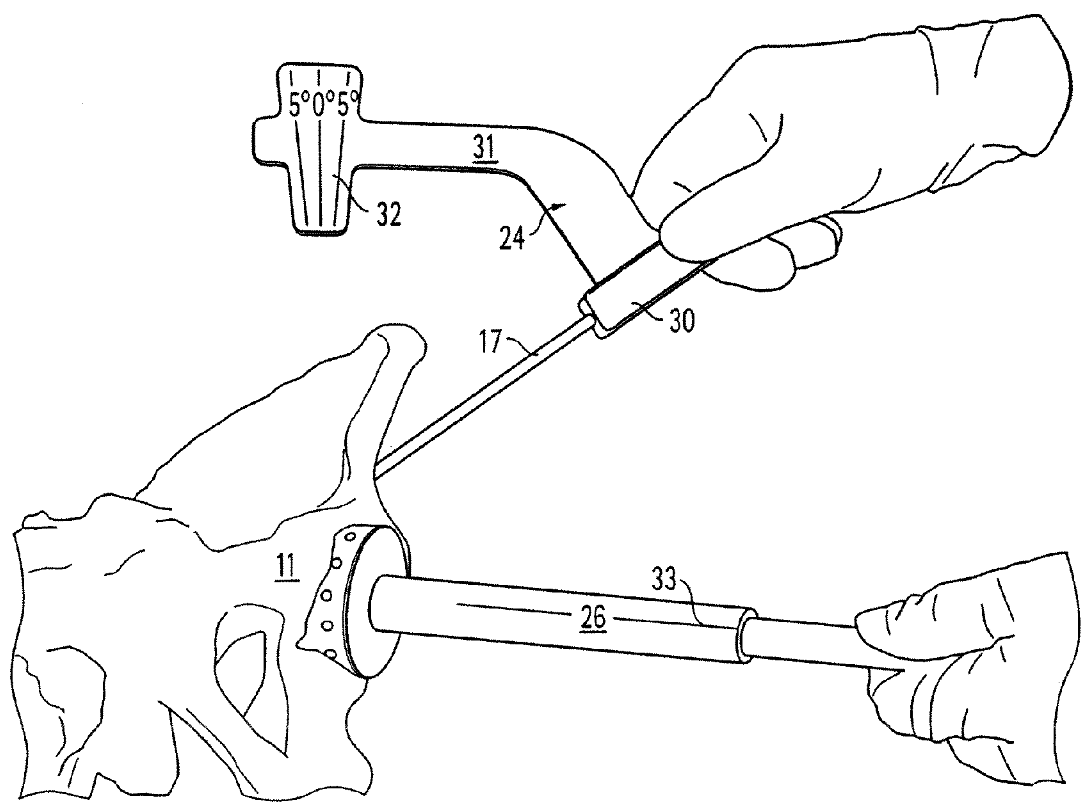
FIG. 6 placement of a bone-milling cutter in the acetabulum, and pushing an orienting template onto the guide rod that is anchored in the bone, to assist orientation of the cutter and/or its drive axle.
Figure 7:
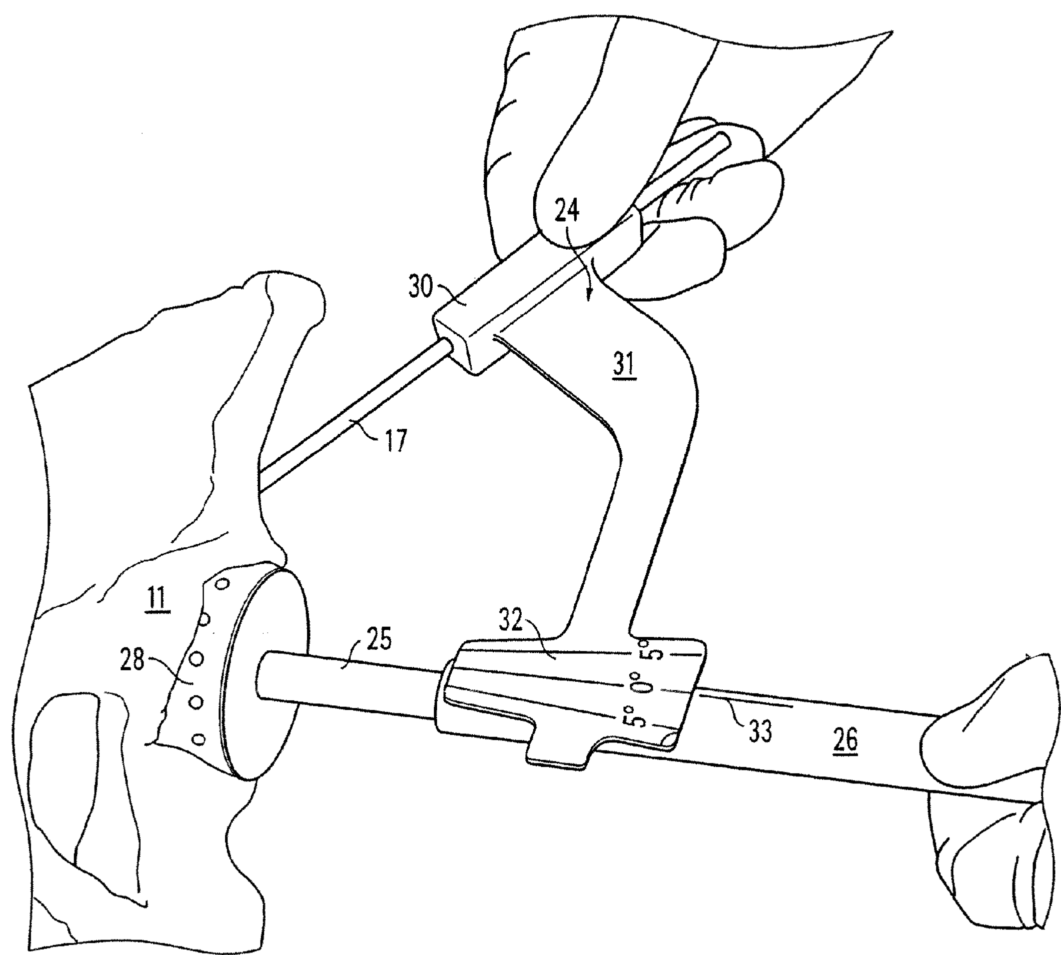
FIGS. 7 and 8 placement of the orienting template and cutter drive axle with respect to one another, and keeping them in this relative position by hand (of the surgeon or an assistant)

Subsequently, as shown in FIGS. 6 and 7, an orienting template 24 is pushed onto the guide rod 17. The orienting template 24 accordingly comprises a guide sleeve fastened to an arm, in this case the angled strap 31. At the free end of the strap 31 a direction plate 32 is formed. This direction plate 32 is provided with marks 33, namely a central zero mark and two tolerance marks at +5°. These marks are identified in FIGS. 6 and 7 by "0°" and "5°".

This orienting template is first used to assist the orientation of a bone-milling cutter with hemispherical cutting head 28 and cutter drive axle 25. To orient the cutting head and its drive axle 25, the template is rotated about the guide rod 17 so as to bring the direction plate 32 into complete, i.e. gap-free contact with the drive axle 25, and then the axle is swivelled parallel to the plate until it is in a position corresponding to a predetermined one of the marks, preferably the zero position "0", as can clearly be seen in FIG. 7.

Figure 8:
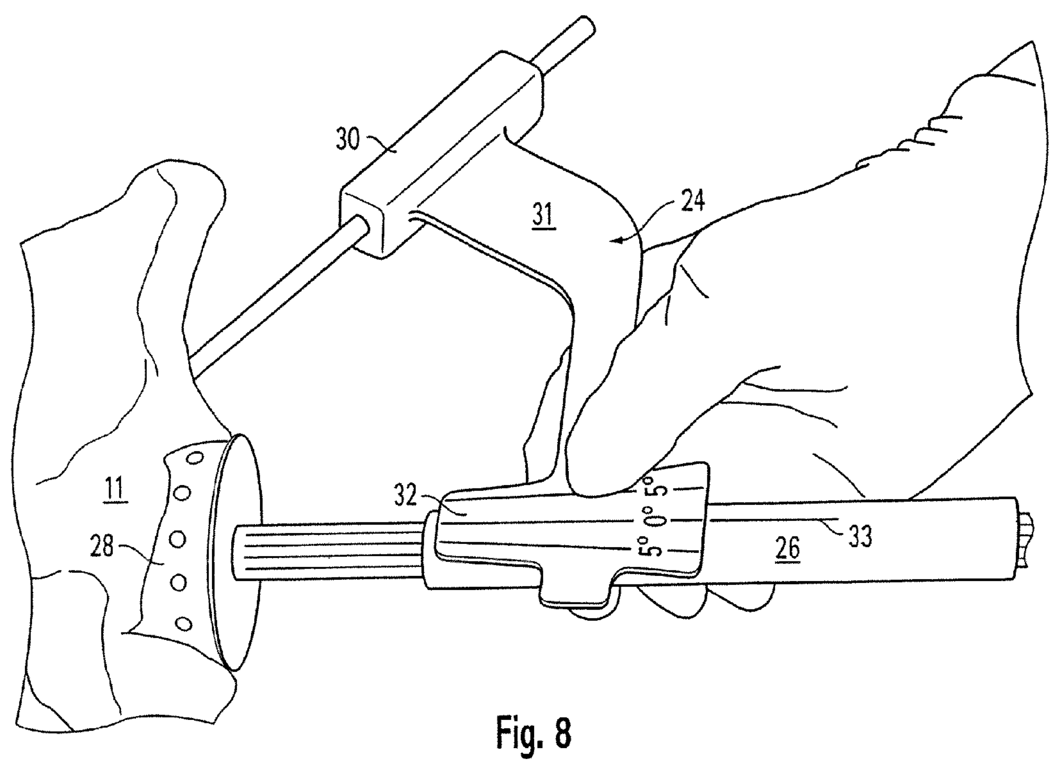

To prevent a collision between direction plate 32 and milling-cutter drive axle 25 while the cutter is in operation, the axle 25 is enclosed in a bush, within which the axle 25 is rotatably seated and onto the surface of which the direction plate 32 can be set and held in gap-free contact during the milling process, as can be seen in FIG. 8.

When the apparatus is positioned according to FIG. 8, the acetabulum can be milled out in the conventional manner. Thanks to the guide rod and the orienting template 24, the hemispherical cutting head 28 is in a position that matches the previously adjusted, anatomically correct position of the manipulation cup 20.

In order to better adjust the cutter drive axle 25 to the zero position, the bush 26 likewise bears a mark 33, a line extending in the long direction. This mark is preferably brought into alignment with the zero mark "0" on the direction plate 32. Thereafter the milling process can be carried out, to produce a suitable bearing socket into which the prosthesis cup can be inserted. Finally, the prosthesis cup is either screwed into this bearing socket or anchored there by so-called "press-fitting".

Figure 9:
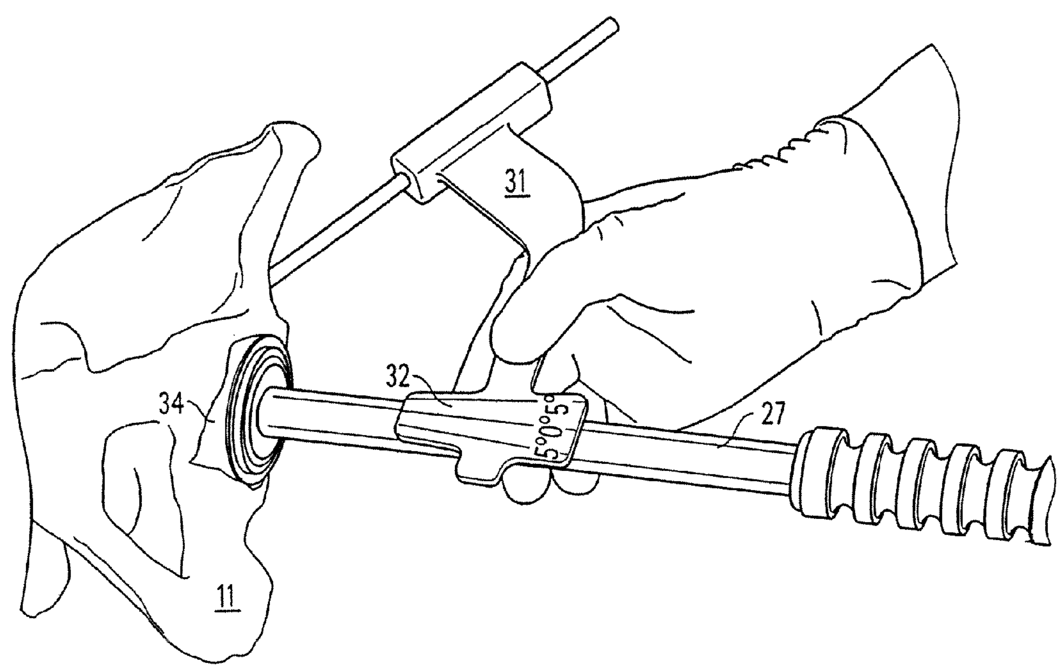
FIG. 9 placement of the orienting template and cup impact instrument with respect to one another, in accordance with the relative positions of orienting template and cutter drive axle as shown in FIGS. 7 and 8.

After milling of the bearing socket in the acetabulum has been completed, the impact instrument 35 (already shown in FIG. 10) is used to hammer in the prosthesis cup 34 that is to be permanently implanted. In this process, of course, care must also be taken that the impact against the prosthesis cup is such that the cup's final position corresponds to that of the manipulation cup 20. Hence the cup impact instrument 27 must be oriented similarly to the bone-milling cutter, i.e. to the cutter's drive axle. The corresponding orientation of the impact instrument 27 is illustrated in FIG. 9. Here, again, the axial structure connecting the impact head to the struck end of the instrument is brought into gap-free contact with the direction plate 32, preferably in alignment with the same marking as was the cutter drive axle. Then it is ensured that when the prosthesis cup 34 is hammered into the previously milled-out bearing socket in the acetabulum, it will be in the anatomically correct orientation.

Figure 11:
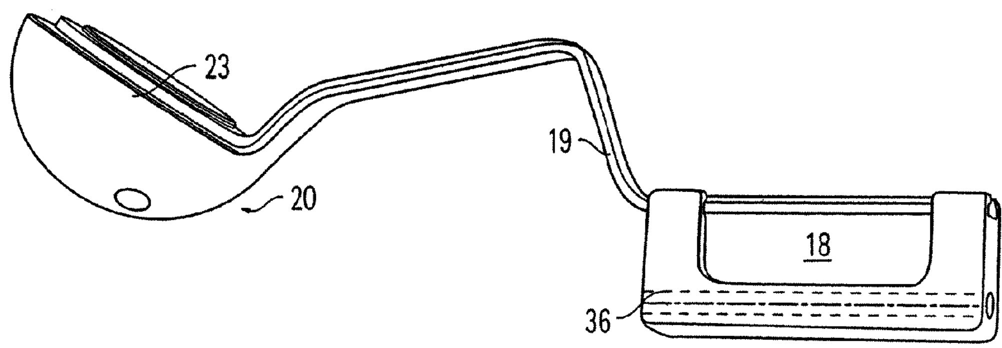
FIG. 11 the manipulation cup together with the guide device for a guide rod that can be anchored in the bone, viewed in perspective.

In FIG. 11 the manipulation cup with guide block for the guide rod 17 is shown again, now in perspective side view. The guide bore in the guide element 30 is indicated by dashed lines and identified by the numeral 36. The guide element 30, as can be seen in FIG. 10 as well as FIG. 5, can be detached from the holder strap 19. The connection between holder strap 19 and guide block is preferably implemented by a catch connector.

Figure 12:
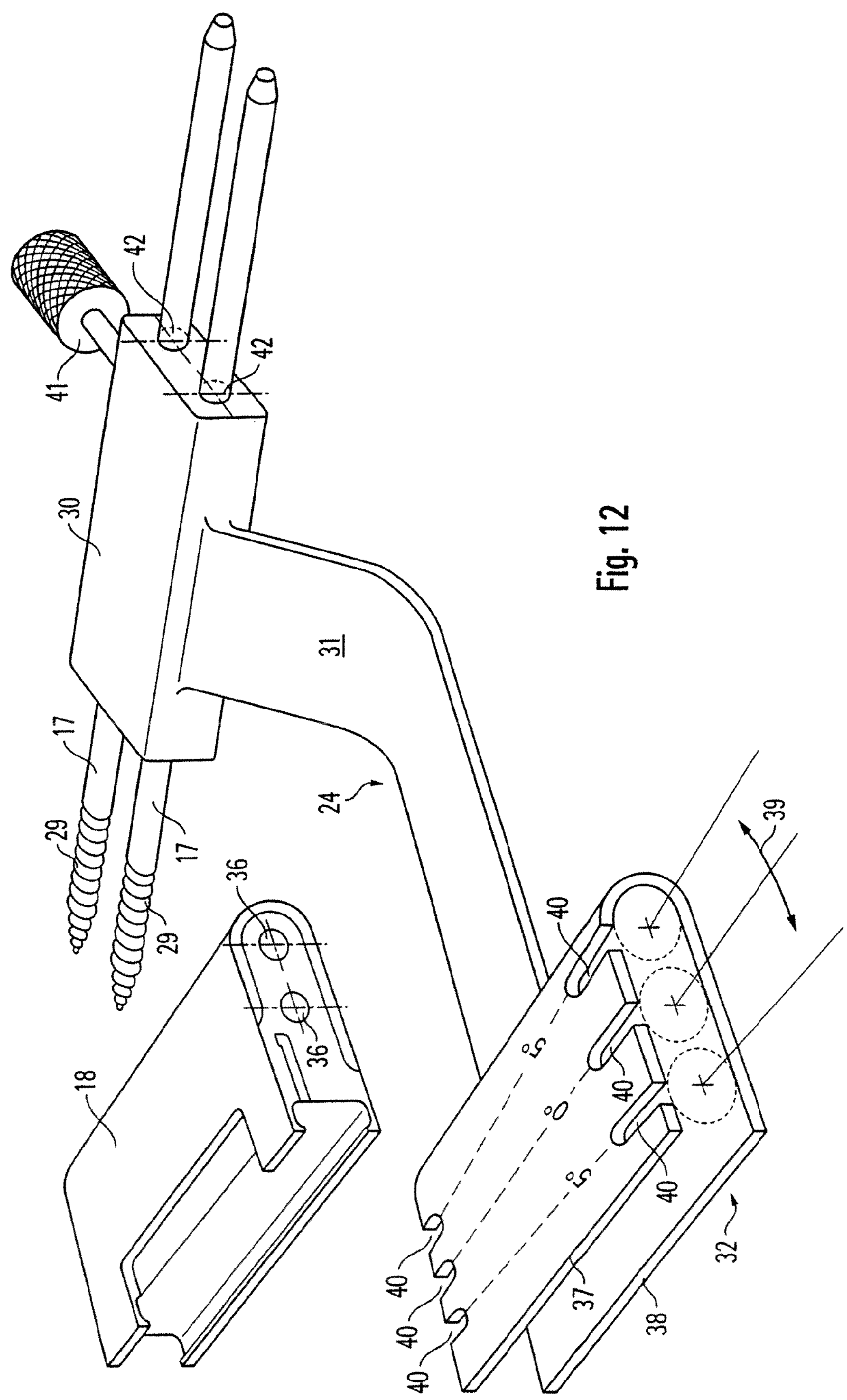
FIG. 12 a modified embodiment of an orienting template, viewed in perspective.

With reference to FIG. 12 a modified embodiment of an orienting template 24 is described, which is distinguished firstly by the fact that the guide element 30 comprises two through-bores 42 to receive two guide rods 17 that extend parallel to one another. Another distinguishing feature of the orienting template 24 shown in FIG. 12 is that the direction plate 32 is bent into a U shape, the space between the two plate limbs 37, 38 serving as a receptacle for the milling-cutter drive axle 25 and/or the cup impact instrument 27. Hence these instruments can be pivoted only in a single plane, parallel to the two plate limbs 37, 38 between which they are held, as indicated by the double-headed arrow 39 in FIG. 12. The arrangement of the two guide rods unambiguously determines the position of the orienting template 24 relative to the acetabulum. Then all that is required of the surgeon is to position the cutter drive axle 25 and/or the cup impact instrument 27 between the two plate limbs 37, 38 in a plane parallel thereto. To facilitate this positioning, recesses 40 are provided in the end faces of the upper plate limb 37. These correspond to the previously mentioned “0” and “±5°” marks.

The guide element 30 additionally comprises a fixing screw 41 to fix the orienting template 24 to the guide rods 17. Because two guide rods 17 are used here, it is of course also necessary for the guide block 18 associated with the manipulation cup 20 to be constructed with two through-bores 42 for the guide rods 17, as is likewise illustrated in FIG. 12.

The embodiment according to FIG. 12—as explained above—permits correction of the angle of the cutter drive axle and/or the cup impact instrument to be carried out only in one plane. The guide rods 17 can be have different lengths. They preferably, as in previous embodiments, have a screw thread 29 at the end toward the bone.

It is obvious that after the prosthesis cup 34 has been put into place, the guide rods 17 must be removed from the bone. Preferably the guide rods 17 consist of so-called “Kirschner wires”.

As mentioned above, the guide block 18 associated with the manipulation cup must also obviously be adapted so that it can be used with two guide rods 17 (two through-bores 36 in the guide block 18 to receive the rods 17, as also shown in FIG. 12).

The manipulation joint head with manipulation rasp must be removed from the femur and replaced by the permanent hip shaft with its joint head. Then the hip joint can be reassembled in the conventional manner. Because of the manipulation and orientation procedures described above, it is then ensured that there will be no collision between the neck of the prosthesis and the rim around the opening of the prosthesis cup 34.

Figure 13:
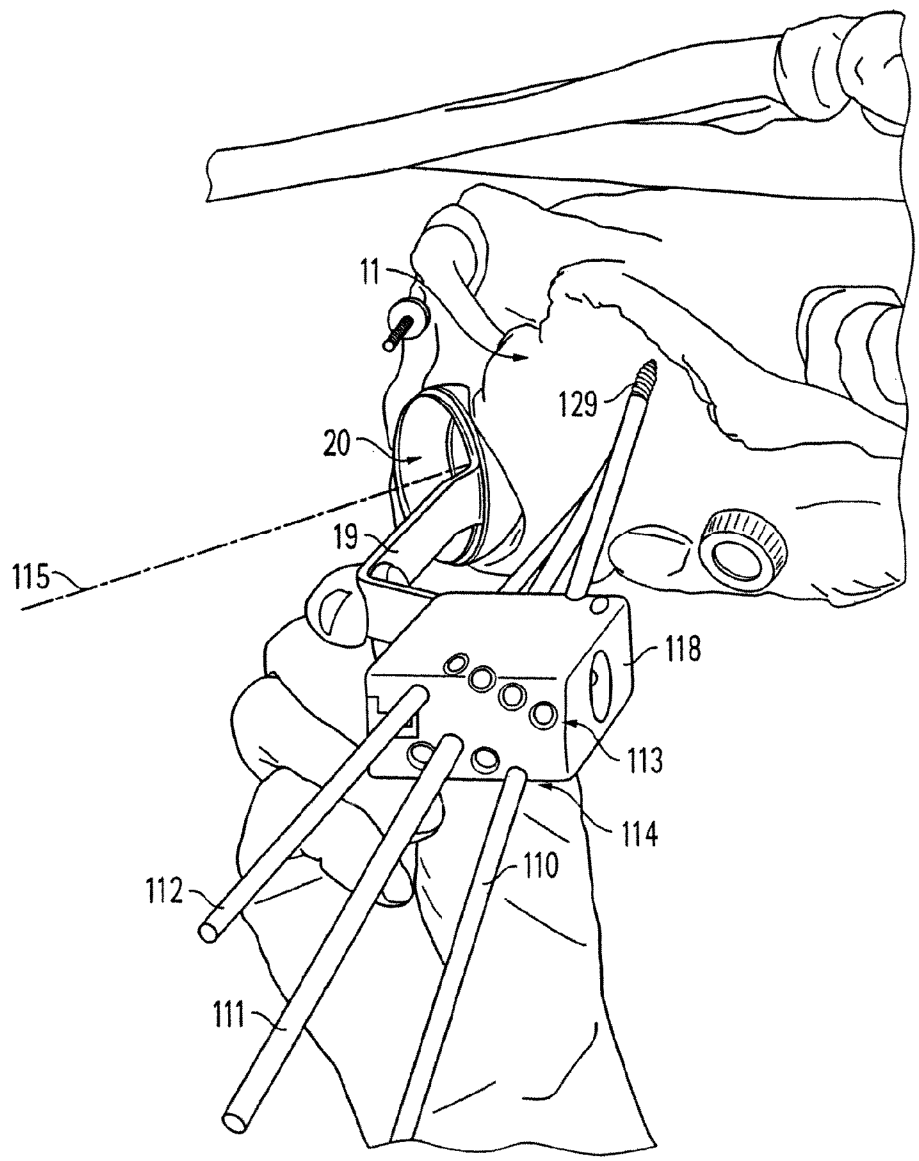
FIG. 13 another embodiment of a device for representing the correct orientation of the manipulation cup, viewed in perspective.

FIG. 13 shows a modified embodiment for a device to represent the oriented position of the manipulation cup 20; this device comprises three fixation rods 110, 111, 112, which extend through a retaining device 118 such that each is at an angle with respect to the others. The fixation rods 110, 111, 112 comprise screw threads 129 on the end sections that are to be anchored in the bone, so that they can be screwed into the bone 11. The retaining device 118 in the present case comprises two rows 113, 114 of holes for the fixation rods 110, so that a sufficient number of holes are available for optimal placement of the fixation rods 110 in the bone 11. The manipulation cup 20 is attached to the retaining device 118 by way of the holder strap 19. Furthermore, it is also possible to connect to the retaining device 118 a guide rod 117, in such a way that the guide rod extends approximately parallel to the central axis 115 of the manipulation cup, indicated in FIG. 13 by the reference numeral 115.

Figure 16:
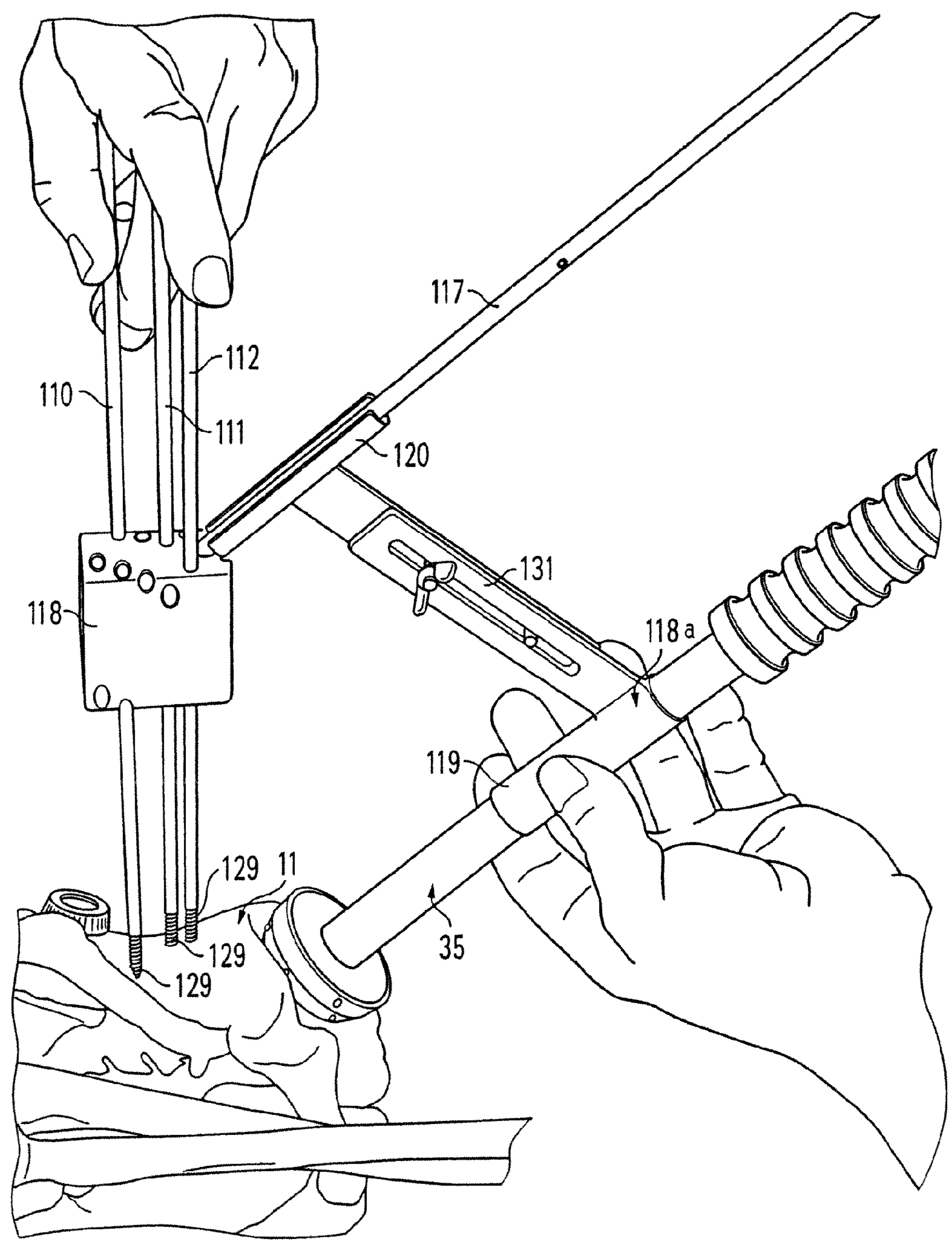
FIG. 16 the arrangement of a guide rod on a manipulation-cup holder, as well as the placement of a guide element on said guide rod for guiding a cup impact instrument, in a position that corresponds to the correctly oriented position of the manipulation cup, in perspective.

To the guide rod 117 there can be attached a guide element **118*a* in the form of a half-sleeve 119. The half-sleeve 119 serves to guide a cutter drive axle 25 (not shown in detail in FIG. 16) or a bush 26 enclosing said axle. It additionally serves to guide or orient a cup impact instrument 35, whereby the guide element 118*a* in the form of a half-sleeve 119 ensures that the orientation of the cutter drive axle and of the cup impact instrument corresponds to that of the manipulation cup 20. In this case the central axis 115** of the manipulation cup coincides with the long axis of the cutter drive axle as well as with the long axis of the cup impact instrument.

The half-sleeve 119 serving as a guide element is connected by way of a flat connector strap 131 to the guide rod 117. The length of the connector strap 131 in the illustrated embodiment can be adjusted. At the end of the connector strap 131 that is associated with the guide rod 117 there is likewise disposed a half-sleeve 120 to serve as an attachment means and sliding shoe. Thus the guide element **118*a* can be put into position on the guide rod 117** in a simple way, and displaced longitudinally thereon.

Figure 14:
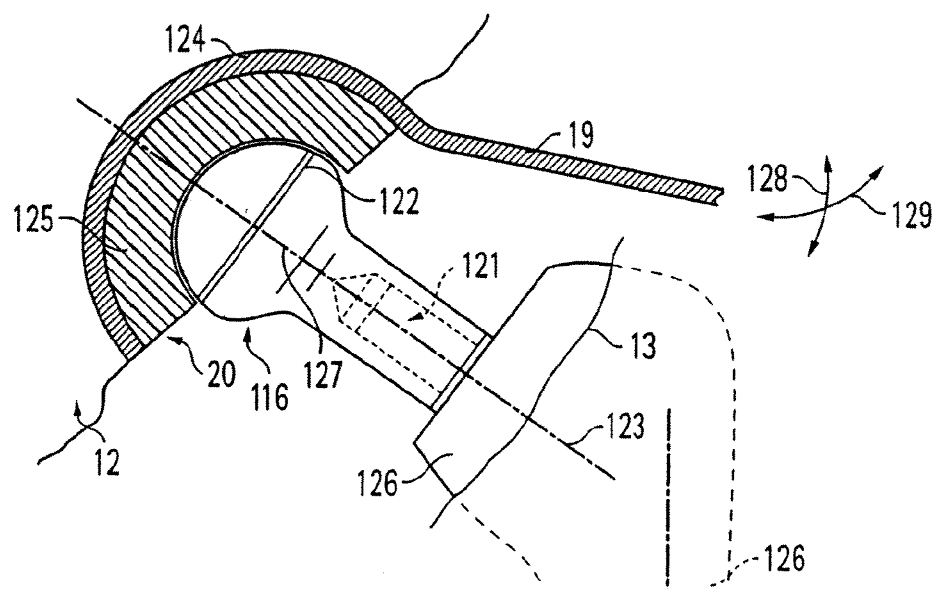
FIG. 14 a second exemplary embodiment of a manipulation joint head in association with a manipulation cup, in schematic section.
Figure 15:
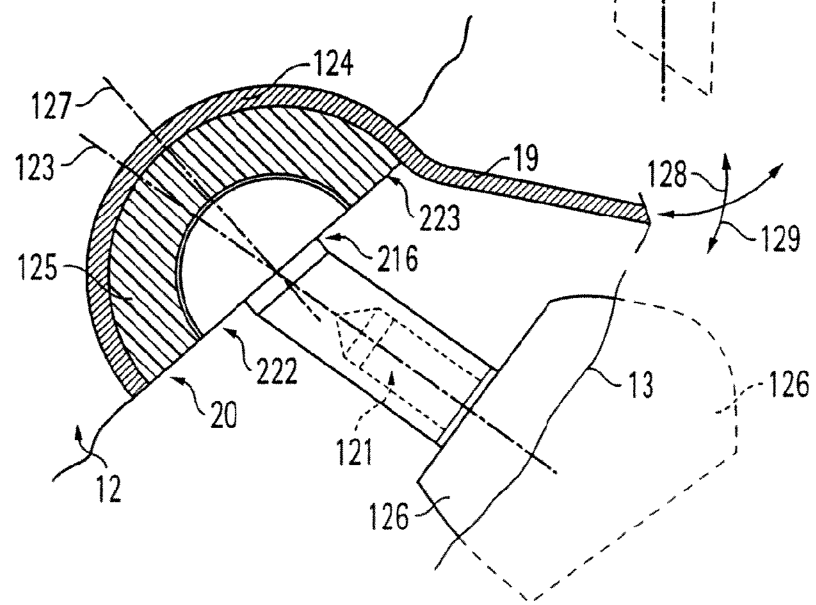
FIG. 15 a third exemplary embodiment of a manipulation joint head in association with a manipulation cup, in schematic section.

FIGS. 14 and 15 show two further, alternative exemplary embodiments of a manipulation joint head 116 and 216, respectively. In both cases the joint heads are mounted on the neck 121 of a manipulation rasp 126. The manipulation rasp 126 has been inserted into the proximal end of a femur 13 (not shown in detail). The long axis of the peg-shaped neck 121 corresponds to the axis of the femoral neck and is identified by the reference numeral 123. The manipulation cup 20 comprises a metallic outer shell 124, onto which has been molded the holder strap 19, as well as an inner shell made of plastic, i.e. an inlay 125. To this extent the structure of the manipulation cup 20 corresponds to that of a prosthesis cup intended for permanent implantation.

In the exemplary embodiment shown in FIG. 14, the means provided for orientation of the manipulation cup 20 in the acetabulum are optical detection means 122. Specifically, the optical detection means 122 is constructed as an indentation or groove extending along the circumference of the spherical part of the manipulation joint head 116. In the present case the path of this groove is perpendicular to the central axis 127 of the joint head, which in the exemplary embodiment according to FIG. 14 coincides with the femoral-neck axis 123.

The indentation 122 extending around the circumference of the spherical part of the manipulation joint head 116 lies within the complementary bearing surface of the manipulation cup 20 when the central axis 127 of the manipulation joint head 116 coincides with the central axis of the manipulation cup. The circumferential indentation 122 does not become visible unless a relative rotation of the manipulation joint head within the manipulation cup 20 occurs. Its invisibility serves as a sign that the manipulation cup 20 is correctly oriented. Preferably the manipulation joint head, i.e. its spherical part, and the manipulation cup comprise markings that correspond to one another, both extending in the circumferential direction, so that the orientation of the manipulation cup about the femoral-neck axis 123 can also be undertaken correctly. The possible movements of the manipulation cup 20, which are those characteristic of a universal joint, are indicated in FIG. 14 by the double-headed arrows 128, 129.

A third exemplary embodiment of means to orient the manipulation cup 20 within the acetabulum 12 is diagrammed in FIG. 15. There the manipulation cup 20 is oriented by the interplay of a circumferential shoulder 222, which extends in a plane perpendicular to the central axis 127 of the joint head, with a receptacle for the neck 121 of the manipulation rasp 126 that extends at an angle to the joint-head central axis 127 (as previously mentioned, the long axis of the neck 121 is parallel to the femoral-neck axis 123).

In this case the manipulation cup 20 has been correctly oriented when said circumferential shoulder 222 is flush with the circumferential ring 223 of the manipulation cup 20, i.e. of the inlay 125.

The two last-mentioned exemplary embodiments thus both comprise optical detection means for orientation of the manipulation cup. They can be handled in a simple manner and function reliably.

In the exemplary embodiment according to FIG. 15, of course, care must be taken that the manipulation joint head is oriented in the prespecified manner with respect to the manipulation rasp 126, i.e. that the joint-head central axis 127 is aimed in a prespecified direction. Only then will it be certain that the objective stated initially is achieved by the final implant.

All the characteristics disclosed in the application documents are claimed as essential to the invention insofar as they are new to the state of the art individually or in combination.

LIST OF REFERENCE NUMERALS

11 Pelvic bone
12 Acetabulum
13 Femur
14 Proximal end of a manipulation rasp
15 Prosthesis neck
16 Manipulation joint head
17 Guide rod
18 Guide block
19 Holder strap
20 Manipulation cup
21 Spherical part of the manipulation joint head
22 Shoulder
23 Opening rim
24 Orienting template
25 Drive axle or shaft for milling cutter
26 Axle bush
27 Cup impact instrument
28 Cutting head
29 Threading
30 Guide sleeve or guide element
31 Angled strap
32 Direction plate
33 Marking
34 Prosthesis cup
36 Guide bore
37 Limb of plate
38 Limb of plate
39 Double-headed arrow
40 Recess
41 Fixing screw
42 Guide bore
110 Fixing rod
111 Fixing rod
112 Fixing rod
113 Row of holes
114 Row of holes
115 Central axis of manipulation cup
116 Manipulation joint head
117 Guide rod
118 Retaining device
**118*a*** Guide element
119 Half-sleeve
120 Half-sleeve
121 Neck of a manipulation rasp
122 Circumferential indentation
123 Neck/femoral-neck axis
124 Outer shell
125 Inlay
126 Manipulation rasp
127 Central axis of joint head
128 Double-headed arrow
129 Double-headed arrow
131 Connector strap
216 Manipulation joint head
222 Circumferential shoulder
223 Circumferential annular surface

The invention claimed is:

1. A method of orienting a bone-milling cutter and an impact instrument for a hip-prosthesis cup in an acetabulum, comprising:
initially positioning a manipulation cup relative to the acetabulum by means of a manipulation joint head,
representing the positioning of the manipulation cup by at least one guide rod or fixation rod that is fixed in a bone,
removing the manipulation cup, and
adjusting a position of both the bone-milling cutter and the impact instrument with respect to either the guide rod itself or a guide rod that is attached to a holding device disposed on at least one fixation rod.

2. The method of claim 1, further comprising engaging a template to the guide rod or fixation rod.

3. The method of claim 2, wherein the engaging the template to the guide rod or fixation rod includes positioning an arm of the template onto the guide rod or fixation rod.

4. The method of claim 2, further comprising using the template to orient a cutting head of the bone-milling cutter in such a way that an orientation of the cutting head matches an orientation of the manipulation cup determined during the positioning.

5. The method of claim 2, further comprising using the template to orient the impact instrument in such a way that an orientation of an impact head of the impact instrument matches an orientation of the manipulation cup determined during the positioning.

6. The method of claim 1, further comprising screwing the guide rod into the bone after the positioning of the manipulation cup relative to the acetabulum.

7. The method of claim 1, further comprising representing the positioning of the manipulation cup by at least two guide rods that are fixed in the bone.

8. A method of orienting a bone-milling cutter and an impact instrument for a hip-prosthesis cup in an acetabulum, comprising:
positioning a manipulation cup in an acetabulum at a desired orientation;
fixing a guide rod in a bone, with a guide device attached to the manipulation cup;
removing the manipulation cup;
engaging a template to the guide rod; and
aligning the bone-milling cutter with the template such that an orientation of the bone-milling cutter matches the desired orientation of the manipulation cup; and
aligning the impact instrument with the template such that an orientation of the impact instrument matches the desired orientation of the manipulation cup.

9. The method of claim 8, wherein the positioning the manipulation cup in the acetabulum includes positioning a manipulation joint head attached to a femur relative to the manipulation cup.

10. The method of claim 8, wherein the guide device attached to the manipulation cup includes a guide bore, and wherein the fixing the guide rod in the bone includes passing the guide rod through the guide bore of the guide device after the positioning of the manipulation cup in the acetabulum at the desired orientation.

11. The method of claim 10, wherein the fixing the guide rod in the bone further includes screwing the guide rod in the bone after the positioning of the manipulation cup in the acetabulum at the desired orientation.

12. The method of claim 8, wherein the template includes a direction plate provided with a marking corresponding to the desired orientation of the manipulation cup, and wherein the aligning the bone-milling cutter with the template includes aligning a cutter drive axle of the bone-milling cutter with the marking of the direction plate.

13. The method of claim 8, further comprising fixing a second guide rod in the bone, with the guide device attached to the manipulation cup; and wherein the engaging includes engaging the template to both of the guide rods.

14. The method of claim 8, wherein the guide device attached to the manipulation cup includes at least two guide bores, including a first guide bore and a second guide bore, wherein the fixing the guide rod in the bone includes passing a first guide rod through the first guide bore of the guide device and into engagement with the bone and passing a second guide rod through the second guide bore of the guide device and into engagement with the bone.

15. A method of orienting a bone-milling cutter and an impact instrument for a hip-prosthesis cup in an acetabulum, comprising:

positioning a manipulation cup in an acetabulum at a desired orientation, wherein the manipulation cup has a guide device attached thereto;

fixing at least one guide rod in a bone and engaging the guide rod to the guide device;

removing the manipulation cup;

engaging a template to the guide rod;

aligning the bone-milling cutter with the template such that an orientation of the bone-milling cutter matches the desired orientation of the manipulation cup;

milling a bearing socket in the acetabulum;

removing the bone-milling cutter; and aligning the impact instrument with the template such that an orientation of the impact instrument matches the desired orientation of the manipulation cup.

16. The method of claim 15, wherein the engaging the template to the guide rod includes positioning an arm of the template onto the guide rod.

17. The method of claim 15, wherein the fixing at least one guide rod in the bone includes fixing a first guide rod in the bone and fixing a second guide rod in the bone; and further comprising engaging each of the first and second guide rods to the guide device.

18. The method of claim 17, further comprising engaging the template to each of the first and second guide rods.

19. The method of claim 15, wherein the bone-milling cutter includes a cutter drive axle and a bushing positioned about the cutter drive axle, and wherein the milling the bearing socket in the acetabulum includes maintaining complete, gap-free contact between the bushing and the template.

20. The method of claim 15, wherein the guide device includes at least one guide bore, and wherein the fixing at least one guide rod in the bone includes passing at least one guide rod through the at least one guide bore and into engagement with the bone.

* * * * *